(12) United States Patent
Di-Fabio et al.

(10) Patent No.: US 6,479,488 B1
(45) Date of Patent: Nov. 12, 2002

(54) TETRAHYDROQUINOLINE DERIVATIVES AS EAA ANTAGONISTS

(75) Inventors: Romano Di-Fabio, Verona (IT); Alessandra Pasquarello, Verona (IT); Fabio Maria Sabbatini, Verona (IT)

(73) Assignee: Glaxo Wellcome SpA, Verona (IT)

( * ) Notice: Subject to any disclaimer, the term of this patent is extended or adjusted under 35 U.S.C. 154(b) by 183 days.

(21) Appl. No.: 09/147,568

(22) PCT Filed: Aug. 14, 1997

(86) PCT No.: PCT/EP97/04440
§ 371 (c)(1),
(2), (4) Date: Oct. 30, 2000

(87) PCT Pub. No.: WO98/07704
PCT Pub. Date: Feb. 26, 1998

(30) Foreign Application Priority Data

Aug. 17, 1996 (GB) .............................. 96173059

(51) Int. Cl.$^7$ ................... A61K 31/47; A61K 31/5377; C07D 215/48; C07D 413/12; A61P 25/00
(52) U.S. Cl. ................... 514/235.2; 514/311; 514/314; 514/235.5; 544/128; 546/165
(58) Field of Search .................. 546/165; 544/128; 514/311, 314, 235.2

(56) References Cited

FOREIGN PATENT DOCUMENTS

| EP | 0 386 839 A | 9/1990 |
| WO | WO97 12870 A | 4/1997 |

OTHER PUBLICATIONS

Carling et al., Bioorganic & Medicinal Chemistry Letters, 3(1): 65–70 (1993).

Primary Examiner—Evelyn Mei Huang

(74) Attorney, Agent, or Firm—Bacon & Thomas

(57) ABSTRACT

Compounds of formula (I) or salt, or metabolically labile ester thereof wherein R represents a group selected from halogen, alkyl, alkoxy, amino, alkylamino, dialkylamino, hydroxy, trifluoromethoxy, nitro, cyano, $SO_2R_2$ or $COR_2$ wherein $R_2$ represents hydroxy, methoxy, amino, alkylamino or dialkylamino; m is zero or an integer 1 or 2; $R_1$ represents cyano or the group $(CH_2)nCN$, $—CH=CHR_3$, $CH_2)nNHCOCH_2R_4$ or $O(CH_2)pNR_5R_6$; $R_3$ represents cyano or the group $COR_7$; $R_4$ represents alkoxy or a group $NHCOR_8$; $R_5$ and $R_6$ each represent independently hydrogen or alkyl, or $R_5$ and $R_6$ together with the nitrogen atom to which they are attached represent a heterocyclic group, or $R_5$ is hydrogen and $R_6$ is the group $COR_9$; $R_7$ represents an alkoxy, amino or hydroxyl group; $R_8$ represents a hydrogen atom or optionally substituted alkyl, alkoxy, aryl, or heterocyclic group; $R_9$ is the group $R_8$ or the group $NR_{10}R_{11}$ wherein $R_{10}$ represents hydrogen or alkyl group; $R_{11}$ represents optionally substituted alkyl, aryl, heterocyclic or cycloalkyl group; n is zero or an integer from 1 to 4, p is an integer from 2 to 4, processes for their preparation and to their use in medicine.

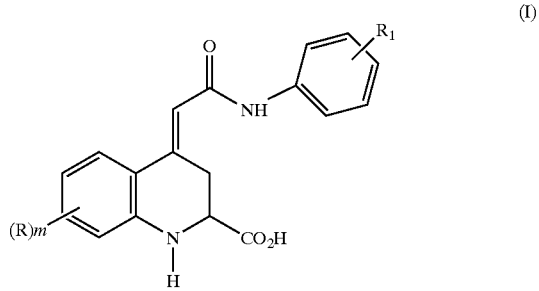

11 Claims, No Drawings

TETRAHYDROQUINOLINE DERIVATIVES AS EAA ANTAGONISTS

This application is a 371 of PCT/EP97/04440, filed on Aug. 14, 1997.

This invention relates to 1,2,3,4 tetrahydroquinoline derivatives, to processes for their preparation, to pharmaceutical compositions containing them and to their use in medicine. In particular, it relates to 1,2,3,4 tetrahydroquinoline derivatives which are potent and specific antagonists of excitatory amino acids.

EPA0386839 describes 1,2,3,4-tetrahydroquiolines possessing at least one substituent at the 4 position and an acidic group at the 2 position and which are specific antagonists of N-methyl-D-aspartate (NMDA) receptors.

Carling et al, Bioorganic and Medicinal Chemistry Letters Vol 13 pp 65–70 1993 teaches 4-substituted-2-carboxy tetrahydroquinolines having good in vitro affinity for the glycine modulatory site of the NMDA receptor complex but at best only weak in vivo activity. More particularly it teaches that such derivatives substituted at the 4 position by the group $CH_2CO_2H$ or $CH_2CONHPh$ have little or no in vivo activity when administered systemically (ip).

We have found a novel group of 4 substituted 2-carboxy-tetrahydroquinoline derivatives which not only have a good in vitro affinity for the strychnine insensitive glycine binding site associated with the NMDA receptor complex but also good in vivo activity when administered systemically eg intravenously (iv).

Thus the present invention provides a compound of formula (I)

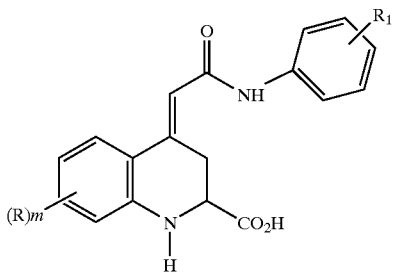

(I)

or a salt, or metabolically labile ester thereof wherein R represents a group selected from halogen, alkyl, alkoxy, amino, alkylamino, dialkylamino, hydroxy, trifluoromethyl, trifluoromethoxy, nitro, cyano, $SO_2R_2$ or $COR_2$ wherein $R_2$ represents hydroxy, methoxy, amino, alkylamino or dialkylamino; m is zero or an integer 1 or 2;

$R_1$ represents a group $(CH_2)nCN$, $-CH=CHR_3$, $(CH_2)nNHCOCH_2R_4$ or $O(CH_2)pNR_5R_6$; $R_3$ represents cyano or the group $COR_7$;

$R_4$ represents alkoxy or a group $NHCOR_8$;

$R_5$ and $R_6$ each represent independently hydrogen or alkyl, or $R_5$ and $R_6$ together with the nitrogen atom to which they are attached represent a heterocyclic group, or $R_5$ is hydrogen and $R_6$ is the group $COR_9$;

$R_7$ represents an alkoxy, amino or hydroxyl group;

$R_8$ represents a hydrogen atom or optionally substituted alkyl, alkoxy, phenyl, heteroaryl or heterocyclic group;

$R_9$ is the group $R_8$ or the group $NR_{10}R_{11}$ wherein $R_{10}$ represents hydrogen or alkyl group;

$R_{11}$ represents optionally substituted alkyl, phenyl, heteroaryl, heterocyclic or cycloalkyl group;

n is zero or an integer from 1 to 4; p is an integer from 2 to 4.

In compounds of formula (I) the exocyclic double bond is in the trans (E) configuration.

For use in medicine the salts of the compounds of formula (I) will be physiologically acceptable thereof. Other salts however may be useful in the preparation of the compounds of formula (I) or physiologically acceptable salts thereof. Therefore, unless otherwise stated, references to salts include both physiologically acceptable salts and non-physiologically acceptable salts of compounds of formula (I).

Suitable physiologically acceptable salts of compounds of the invention include base addition salts and where appropriate acid addition salts.

Suitable physiologically acceptable base addition salts of compounds of formula (I) include alkali metal or alkaline earth metal salts such as sodium, potassium, calcium, and magnesium, and ammonium salts, formed with amino acids (e.g. lysine and arginine) and organic bases (e.g. procaine, phenylbenzylamine, ethanolamine diethanolamine and N-methyl glucosamine).

The compounds of formula (I) and/or salts thereof may form solvates (e.g. hydrates) and the invention includes all such solvates.

Compounds of formula (I) and in particular the base addition salts thereof e.g. sodium salt have been found to have an advantageous profile of solubility in water.

The term alkyl as used herein as a group or part of a group refers to a straight or branched chain alkyl group containing from 1 to 4 carbon atom examples of such groups including methyl, ethyl, propyl, isopropyl, n-butyl, isobutyl, secondary butyl or tertiary butyl.

The term optionally substituted alkyl as used herein refers to an alkyl group as defined above and which is substituted by one or more hydroxy, carboxyl, and amino groups.

The term halogen refers to a fluorine, chlorine, bromine or iodine atom.

The term heteroaryl refers to a 5 or 6 membered heteroaryl group in which the 5-membered heteroaryl group contains 1 or 2 heteroatoms selected from oxygen sulphur or nitrogen and the 6-membered heteroaryl group containing 1 or 2 nitrogen atoms.

Examples of suitable heteroaryl groups include furanyl, thiophenyl, imidazolyl, thiazolyl, oxazolyl, pyridinyl, and pyrimidinyl.

The term optionally substituted phenyl refers to a phenyl group substituted with up to 3 substituents selected from halogen, C1–4 alkyl, C1–4 alkoxy, amino,alkylamino, hydroxy, trifluoromethyl, carboxyl or methoxycarbonyl.

The term cycloalkyl refers to a $C_{3-7}$cycloalkyl group which may optionally be substituted by 1 or 2 $C_{1-4}$ alkyl groups e.g cyclopropyl, cyclobutyl,cyclopentyl, cyclohexyl cycloheptyl or 2-methylcyclohexyl.

The term optionally substituted heterocyclic group refers to 5–7 membered saturated heterocyclic groups containing one or two heteroatoms selected from oxygen, sulphur or nitrogen. Examples of suitable groups containing a single heteroatom include tetrahydropyranyl e.g. 4-tetrahydropyranyl, pyrrolidinyl e.g 2 or 3 pyrrolidinyl, piperidinyl e.g 4- or 3-piperidinyl and N-substituted derivatives therefore (e.g. N-alkyl such as e.g. methyl or N-acyl such as N-alkanoyl e.g. acetyl or N-alkoxycarbonyl e.g. ethoxycarbonyl), piperidino or pyrrolidino. Examples of suitable groups containing 2 heteroatoms include morpholino, thiomophlino or piperazino.

When $R_5$ and $R_6$ together with the nitrogen atom to which they are attached represent an heterocyclic group this is a saturated 5–7 membered ring optionally containing an additional heteroatom selected from oxygen, sulphur or nitrogen.

Examples of such groups include morpholino, 2,6 dimethylmorpholino, piperidino, pyrrolidino, piperazino or N-methylpiperazino.

The compounds of formula(I) possess at least one asymmetric carbon atom (namely the carbon atom occupying the 2 position of the 1, 2, 3, 4 tetrahydroquinoline ring system) and other asymmetric carbon atoms are possible in the groups R and R1. Also when R1 is the group CH=CHR$_3$, the group may exist in the cis or trans configuration or mixtures. It is to be understood that all stereoisomers including enantiomers, diastereoisomers and geometric isomers and mixtures thereof are encompassed within the scope of the present invention.

It will be appreciated that the compounds of formula (I) may be produced in vivo by metabolism of a suitable prodrug. Such prodrugs include for example physiologically acceptable metabolically labile esters of compounds of the general formula (I). These may be formed by esterification, for example of any of the carboxylic acid groups in the parent compound of general formula (I) with, where appropriate, prior protection of any other reactive groups present in the molecule, followed by deprotection if required. Examples of such metabolically labile esters include $C_{1-4}$alkyl esters e.g. methyl or ethyl esters, substituted or unsubstituted aminoalkyl esters (e.g. aminoethyl, 2-(N,N-diethylamino) ethyl, or 2-(4-morpholino)ethyl esters or acyloxyalkyl esters such as, acyloxymethyl or 1-acyloxyethyl e.g. pivaloyloxymethyl, 1-pivaloyloxyethyl, acetoxymethyl, 1-acetoxyethyl, 1-(1-methoxy-1-methyl) ethylcarbonyloxyethyl, 1-benzoyloxyethyl, isopropoxycarbonyloxymethyl, 1-isopropoxycarbonyloxyethyl, cyclohexylcarbonyloxymethyl, 1-cyclohexylcarbonyloxyethyl ester, cyclohexyloxycarbonyloxymethyl, 1-cyclohexyloxycarbonyloxyethyl, 1-(4-tetrahydropyranyloxy)carbonyloxyethyl or 1-(4-tetrahydropyranyl)carbonyloxyethyl.

For compounds of formula (I) m is conveniently 1 or 2 and within these compounds those wherein R is at the 5 and/or 7 position are preferred.

The group R is conveniently a halogen atom, such as bromine or chlorine and preferably is a chlorine atom.

A preferred group of compounds of formula (I) are those wherein m is 2 and R which is at the 5 and 7 position is bromine or more particularly chlorine.

When $R_3$ is the group $COR_7$, $R_7$ is conveniently hydroxyl, amino or $C_{1-4}$alkoxy e.g. methoxy, ethoxy, propoxy, butoxy and t-butoxy.

When $R_4$ is the group $NHCOR_8$, $R_8$ is conveniently hydrogen or $C_{1-4}$alkyl e.g. methyl, ethyl, isopropyl, butyl or isobutyl When $R_1$ is the group $O(CH_2)pNR_5R_6$. Conveniently $R_5$ and $R_6$ each represent hydrogen or $NR_5R_6$ represents a morpholino group, or R5 represents hydrogen and $R_6$ represents $COR_9$ wherein $R_9$ is hydrogen or $C_{1-4}$alkyl or the group $NH_2$;

n is conveniently zero, 1 or 2;

p is conveniently 2.

The group $R_1$ may be in the 2, 3 or 4 position in the phenyl ring and is conveniently at the 3 or 4 position. Preferably $R_1$ is at the 4 position.

A preferred class of compounds are those wherein $R_1$ is the group $(CH_2)_nCN$ (eg. $CH_2CN$), —CH=CHR$_3$ wherein $R_3$ is cyano or $COR_7$ (wherein $R_7$ is $C_{1-4}$ alkoxy(e.g. t-butoxy) or amino), $(CH_2)nNHCOCH_2R4$ (wherein $R_4$ is alkoxy e.g. methoxy or $NHCOR_8$ wherein $R_8$ is hydrogen or $C_{1-4}$alkyl (e.g. isopropyl)) or $O(CH_2)pNR_5R_6$ wherein $R_5$ and $R_6$ are hydrogen (e.g. aminoethoxy) or $NR_5R_6$ represents morpholino (e.g. morpholino ethoxy) or $R_5$ represents hydrogen and $R_6$ is $COR_9$ wherein $R_9$ is hydrogen or $C_{1-4}$alkyl e.g isopropyl. Within this class of compounds n is zero, 1 or 2 and more preferably 1; p is 2, 3 or 4 and more preferably 2.

A particularly preferred class of compounds are those wherein $R_1$ is the group $CH_2CN$, —CH=CHR$_3$ (wherein $R_3$ is $C_{1-4}$alkoxycarbonyl eg butoxycarbonyl, carbamoyl or cyano), $(CH_2)_nNHCOCH_2R_4$ (wherein n is zero and $R_4$ is $C_{1-4}$alkoxy, eg methoxy or $NHCOR_8$ wherein $R_8$ is $C_{1-4}$alkyl eg isopropyl), eg $R_1$ is 2-methoxyacetylamino or isobutyrylamino-methylcarbonylamino, or $R_1$ is $O(CH_2)_pNR_5R_6$ (wherein p is 2, $R_5$ is hydrogen and $R_8$ is $COR_9$ wherein $R_9$ is $C_{1-4}$alkyl eg isopropyl, or $NR_5R_6$ represents a morpholino group) eg $R_1$ is 2-isobutyryl aminoethoxy or 2-morpholino-4-ylethoxy.

Specific preferred compounds of the invention include:

(±) (E) 5,7-Dichloro-4-[4-(2-methoxy-acetylamino)-phenylcarbamoylmethylene]-1,2,3,4-tetrahydro-quinoline-2-carboxylic acid;

(±) (+,−) (E) 5,7-Dichloro-4-[4-(2-isobutyrylamino-methylcarbonylamino)-phenylcarbamoylmethylene]-1,2,3,4-tetrahydro-quinoline-2-carboxylic acid;

and physiologically acceptable salts e.g. sodium salt, metabolically labile esters or enantiomers thereof.

Further specific preferred compounds of the invention include:

(±) (E) 5,7-Dichloro-4-(4-cyanomethyl-phenylcarbamoylmethylene)-1,2,3,4-tetrahydro-quinoline-2-carboxylic acid;

(±) (E,E) 5,7-Dichloro-4-[4-(2-cyano-vinyl)-phenylcarbamoylmethylene]-1,2,3,4-tetrahydro-quinoline-2-carboxylic acid;

(±) (E,E) 4-[4-(2-tert-butoxycarbonyl-vinyl)-phenylcarbamoylmethylene]-5,7-dichloro-1,2,3,4-tetrahydro-quinoline-2-carboxylic acid;

(±) (E,E) 4-[4-(2-carbamoyl-vinyl)-phenylcarbamoylmethylene]-5,7-dichloro-1,2,3,4-tetrahydro-quinoline-2-carboxylic acid;

(±) (E) 5,7-Dichloro-4-[4-(2-isobutyrylamino-ethoxy)-phenylcarbamoylmethylene]-1,2,3,4-tetrahydro-quinoline-2-carboxylic acid;

(±) (E) 5,7-Dichloro-4-[4-(2-morpholin-4-yl-ethoxy)-phenylcarbamoylmethylene]-1,2,3,4-tetrahydro-quinoline-2-carboxylic acid;

and physiologically acceptable salts e.g. sodium salt, metabolically labile esters or enantiomers thereof.

The compounds of formula (I) and/or physiologically acceptable salts thereof are excitatory amino acid antagonists. More particularly they are potent antagonists at the strychnine insensitive glycine binding site associated with the NMDA receptor complex. As such they are potent antagonists of the NMDA receptor complex. These compounds are therefore useful in the treatment or prevention of neurotoxic damage or neurodegenerative diseases. Thus the compounds are useful for the treatment of neurotoxic injury which follows cerebral stroke, thromboembolic stroke, hemorrhagic stroke, cerebral ischemia, cerebral vasospam, hypoglycemia, anaesia, hypoxia, anoxia, perinatal asphyxia cardiac arrest. The compounds are also useful in the treatment of chronic neurodegenerative diseases such as; Huntingdon's disease, Alzheimer's senile dementia, amyotrophic lateral sclerosis, Glutaric Acidaemia type, multi-infarct dementia, status epilecticus, contusive injuries (e.g. spinal cord injury and head injury), viral infection induced neurodegeration (e.g. AIDS, encephalopaties), Down syndrome, epilepsy, schizophrenia, depression, anxiety, pain, migraine, headaches including cluster headaches and or tension headaches, neurogenic bladder, irritative bladder disturbances, drug dependency, including withdrawal symptoms from alcohol, cocaine, opiates, nicotine, benzodiazepine, and emesis.

The potent and selective action of the compound of the invention at the strychnine-insensitive glycine binding site present on the NMDA receptor complex may be readily determined using conventional test procedures. Thus the ability to bind at the strychnine insensitive glycine binding site was determined using the procedure of Kishimoto H et al. J Neurochem 1981, 37 1015–1024. The selectivity of the action of compounds of the invention for the strychnine insensitive glycine site was confirmed in studies at other ionotropic known excitatory amino acid receptors. Thus compounds of the invention were found to show little or no affinity for the kainic acid (kainate) receptor, a-amino-3-hydroxy-5-methyl-4-isoxazole-proprionic acid (AMPA) receptor or at the NMDA binding site.

Compounds of the invention have also been found to inhibit NMDA induced convulsions in mice using the procedure Chiamulera C et al. Psychopharmacology (1990) 102, 551–552.

The ability of compounds of the invention to inhibit pain may be demonstrated in conventional analgesic screens such as those described by J J Bennett and J K Xue, Pain 1988,41,87–107.

The invention therefore provides for the use of a compound of formula (I) and/or physiologically acceptable salt or metabolically labile ester thereof for use in therapy and in particular use as medicine for antagonising the effects of excitatory amino acids upon the NMDA receptor complex.

The invention also provides for the use of a compound of formula (I) and/or a physiologically acceptable salt or metabolically labile ester thereof for the manufacture of a medicament for antagonising the effects of excitatory amino acids upon the NMDA receptor complex.

According to a further aspect, the invention also provides for a method for antagonising the effects of excitatory amino acids upon the NMDA receptor complex, comprising administering to a patient in need thereof an antagonistic amount of a compound of formula (I) and/or a physiologically acceptable salt or metabolically labile ester thereof.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated, the route of administration and the age and the condition of the patient and will be ultimately at the discretion of the attendant physician. In general however doses employed for adult human treatment will typically be in the range of 2 to 800 mg per day, dependent upon the route of administration. Thus for parenteral administration a daily dose will typically be in the range 20–100 mg, preferably 60–80 mg per day. For oral administration a daily dose will typically be within the range 200–800 mg, e.g. 400–600 mg per day.

The desired dose may conveniently be presented in a single dose or as divided doses administered at appropriate intervals, for example as two, three, four or more sub-doses per day.

While it is possible that, for use in therapy, a compound of the invention may be administered as the raw chemical, it is preferable to present the active ingredient as a pharmaceutical formulation.

The invention thus further provides a pharmaceutical formulation comprising a compound of formula (I) or a pharmaceutically acceptable salt or metabolically labile ester thereof together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, inhalation or insufflation, implant, or rectal administration. Parenteral administration is preferred.

Tablets and capsules for oral administration may contain conventional excipients such as binding agents, for example, syrup, accacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; solubilizers such as surfactants for example polysorbates or other agents such as cyclodextrins; and preservatives, for example, methyl or propyl p-hydroxybenzoates or ascorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compounds according to the invention are conveniently delivered in the form of an aerosol spray presentation from pressurised packs, with the use of a suitable propellant, such as dichlorodifluoromethane, tirchlorofluoromethane, dichlorotetrafluoroethane, carbon dioxide or other suitable propellants, such as dichlorodifluoromethane, trichlorofluoromethane, dichloro-tetrafluoroethane, carbon dioxide or other suitable gases, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable carrier such as lactose or starch. The powder composition may be presented in unit dosage form in, for example, capsules or cartridges of e.g. gelatin, or blister packs from which the powder may be administered with the aid of an inhaler or insufflator.

The composition according to the invention may also be formulated as a depot preparation. Such long acting formulations may be administered by implantation (for example subcutaneously or intramuscularly) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The compositions according to the invention may contain between 0.1–99% of the active ingredient, conveniently from 30–95% for tablets and capsules and 3–50% for liquid preparations.

Compounds of general formula (I) and salts thereof may be prepared by the general methods outlined hereinafter. In the following description, the groups R, m, $R_1$ are as defined for the compounds of formula (I) unless otherwise stated.

Compounds of formula (I) may be prepared by the cyclisation of a compound of formula (II) in which $R_{12}$ is a carboxylic protecting group, $R_{13}$ represents a bromine or iodine atom, $R_{14}$ represents hydrogen or a nitrogen protecting group and $R_1$ has the meanings defined in formula(I) or a protected derivative thereof.

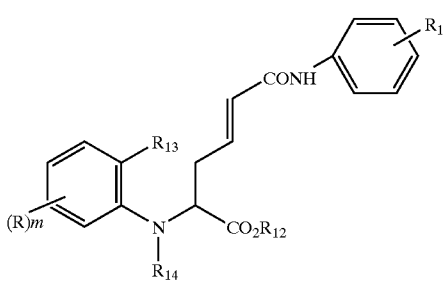

(II)

In one embodiment of this process the reaction may be carried out using a catalytic amount of a Palladium (O) complex such as tetrakis(triphenylphosphine)palladium and a suitable organic base such as trialkylamine e.g triethylamine or inorganic base, e.g. potassium carbonate. The reaction is conveniently carried out in an aprotic solvent such as acetonitrile or dimethylformamide at a temperature with the range of 60° C. to 150° C. followed, where necessary or desired, by subsequent removal of the carboxyl protecting group $R_{12}$ and any protecting group $R_{14}$.

In a further embodiment of the process the reaction is carried out using a catalytic amount of a Pd(II) salt such as: palladium acetate, in the presence of a suitable organic base such as a trialkyl amine e.g. triethylamine and a triarylphosphine such as triphenylphosphine.

The reaction is carried out in an aprotic solvent such as acetonitrile or dimethylformamide and preferably with heating, where necessary or desired, by subsequent removal of the carboxyl protecting group $R_{12}$ and any protecting group $R_{14}$.

Suitable carboxyl protecting groups $R_{12}$ for use in this reaction include alkyl, trichloroalkyl, trialkylsilylalkyl, or arylmethyl groups such as benzyl, nitrobenzyl or trityl.

When $R_{14}$ is nitrogen protecting examples of suitable groups include alkoxycarbonyl e.g. t-butoxycarbonyl, arylsulphonyl e.g. phenysulphonyl or 2-trimethylsilylethoxymethyl.

In a further process of the invention compounds of formula(I), may be prepared by reaction of an activated derivative of the carboxylic acid (III) in which $R_{12}$ is a carboxyl protecting group and $R_{14}$ is hydrogen or a nitrogen protecting group as defined in formula (II)

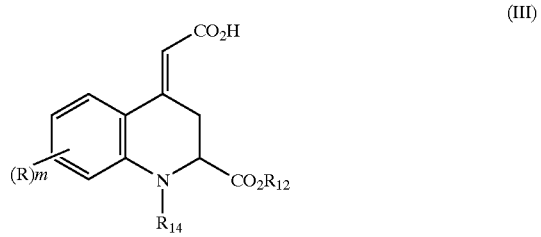

with the amine(IV)

wherein R1 has the meaning defined in formula(I) or are protected derivative thereof, followed where necessary by subsequent removal of the carboxyl protecting group $R_{12}$ and any nitrogen protecting group $R_{14}$.

Suitable activated derivatives of the carboxyl group include the corresponding acyl halide, mixed anhydride, activated ester such as a thioester or the derivative formed between the carboxylic acid group and a coupling agent such as that used in peptide chemistry, for example carbonyl diimidazole or a diimide such as dicyclohexylcarbodiimide.

The reaction is preferably carried out in an aprotic solvent such as a hydrocarbon, a halohydrocarbon, such as dichloromethane or an ether such as tetrahydrofuran.

Suitable carboxyl protecting groups $R_{12}$ for use in this reaction include alkyl, trichloroalkyl, trialkylsilylalkyl, or arylmethyl groups such as benzyl, nitrobenzyl or trityl.

When $R_{14}$ is nitrogen protecting examples of suitable groups include alkoxycarbonyl eg. t-butoxycarbonyl, arylsulphonyl e.g. phenysulphonyl or 2-trimethylsilylethoxymethyl.

The activated derivatives of the carboxylic acid (III) may be prepared by conventional means. Particularly suitable activated derivatives for use in this reaction are thioesters such as that derived from pyridine-2-thiol. These esters may conveniently be prepared by treating the carboxylic acid (III) with 2,2'-dithiopyridine and triphenylphosphine in a suitable aprotic solvent such as an ether e.g. tetrahydrofuran, a halohydrocarbon e.g. dichloromethane, an amide e.g. N,N-dimethylformamide or acetonitrile.

Compounds of formula (II) may be prepared from compound of formula (V) in which $R_{12}$ is a carboxyl protecting group and $R_{14}$ is hydrogen or a nitrogen protecting group as defined in formula (II) and $R_{13}$ represents a bromine or iodine atom

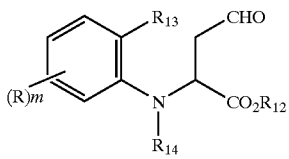
(V)

by rection with an appropriate phosphorus reagent capable of converting the group CHO into the group:

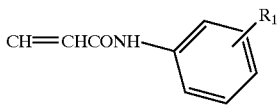

followed, where necessary or desired, by removal of the carboxyl protecting group $R_{12}$ and nitrogen protecting group $R_{14}$.

In one embodiment of this process the reaction may be carried out using a phoshorus ylide of formula (VI)

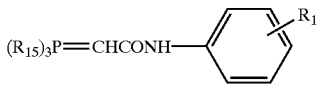
(VI)

wherein $R_{15}$ is an alkyl or phenyl group and $R_1$ has the meanings defined in formula(I) or a protected derivative thereof.

The reaction is carried out in an aprotic solvent such as acetonitrile or dimethylformamide at a temperature ranging from $-10°$ C. to the reflux temperature of the solvent.

Compounds of formula (V) may be prepared by ozonization of the allyl compound of formula (VII) in which $R_{12}$ is a carboxyl protecting group, $R_{14}$ is hydrogen or a nitrogen protecting group as defined above and $R_{13}$ represents a bromine or iodine atom.

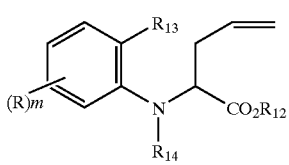
(VII)

The reaction may be effected by passing a stream of ozone into a solution of compound of formula (VII) in the presence of dimethyl sulphide or triphenylphosphine in a suitable solvent such as halohydrocarbon e.g dichloromethane at low temperature e.g $-78°$ C.

Compounds of formula (VII) wherein $R_{14}$ is hydrogen atom and $R_{12}$ is carboxyl protecting group as defined above may be prepared by reaction of the amine(VIII) wherein $R_{13}$ represents a bromine or iodine atom with the aldehyde (IX) in which $R_{12}$ is carboxyl protecting group

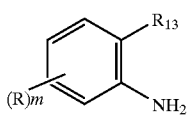
(VIII)

(IX)

followed by addition of allyltributyltin in the presence of Lewis acid such as titanium(IV) chloride or boron trifluoride etherate. The reaction conveniently takes place in a solvent such as hydrocarbon e.g toluene or halogenated hydrocarbon e.g. dichloromethane at a temperature ranging from $-78°$ C. to room temperature. Compounds of formula (VII) in which $R_{14}$ is nitrogen protecting group and $R_{12}$ is carboxyl protecting group as defined above may be prepared from the compound of formula(VII) wherein $R_{14}$ represents hydrogen atom using conventional procedure for preparing such protected nitrogen atom.

Compounds of formula (III) may be prepared by the cyclisation of a compound of formula (X) in which $R_{12}$ is a carboxylic protecting group, $R_{13}$ represents a bromine or iodine atom, $R_{14}$ represents hydrogen or a nitrogen protecting group as defined above, and $R_{16}$ represents a suitable carboxyl protecting group such as a t-butyl group

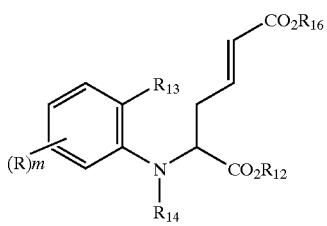
(X)

using similar reaction conditions for those described above for the reaction of compounds of formula (II), followed by removal of the carboxyl protecting group $R_{16}$ and where necessary or desired by removal of the nitrogen protecting group $R_{14}$ The carboxyl protecting group may be removed by conventional procedures. Thus when $R_{16}$ is a t-butyl group it may be removed by reaction with formic acid.

Compounds of formula (X) may be prepared from compound of formula(V) and a phosphourus ylide $(R_{15})_3P=CHCO_2R_{16}$ in which $R_{15}$ has the meaning defined in formula (VI) and $R_{16}$ is as defined above, using similar reaction condition for those described above for the reaction of (V) with compound of formula (VI).

In a further process of the invention compounds of formula(X) may be prepared by reaction of the imino compound(XI), in which $R_{12}$ is a carboxylic protecting group, $R_{13}$ represents a bromine or iodine atom, with silane derivatives (XII)

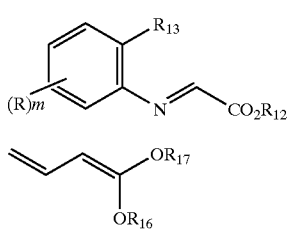
(XI)

(XII)

wherein R17 is a trialkylsilyl group such as tri($C_{1-4}$)alkyl group. Example of suitable trialkylsilyl groups include trimethylsilyl and ter-butyldimethylsilyl and $R_{16}$ represents a suitable protecting group such as t butyl group, in the presence of Lewis acid such as stannic chloride or stannic bromide.

The reaction is conveniently carried out at temperature ranging from −78° C. to room temperature in an aprotic solvent such as halohydrocarbons i.e dichloromethane, or aromatic hydrocarbons such as toluene, chlorobenzene or fluorobenzene.

Compounds of formula(XI) may be prepared by reaction of compounds of formula(VIII) and (IX) wherein $R_{13}$ represents a bromine or iodine atom with the aldehyde (IX) in which $R_{12}$ is carboxyl protecting group

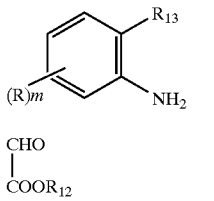

(VIII)

(IX)

The reaction conveniently takes places in a solvent such as hydrocarbon e.g toluene at reflux temperature in the presence of a drying agent such as magnesium sulphate or sodium sulphate.

Compounds of formula (IV), (VI), (VIII) (IX) and (XII) are either known compounds or may be prepared by analogous methods to those used for known compounds.

Specific enantiomers of the compounds of formula(I) may be obtained by resolution of the racemic compounds using conventional procedures such as salts formation with a suitably optically active amine i.e. (R)-α-phenylethylamine, (S) α-phenylethylamine, brucine, cinconidine, quinine, followed by separation of the two diastereoisomer salts obtained and regeneration of the free acid. The two diastereoisomeric salts may be conveniently separated by conventional means such as fractional crystallisation.

Alternatively the required enantiomer may be obtained from racemic compounds of formula(I) by use of chiral HPLC procedures.

In a further process of the invention the required enantiomer may be prepared by esterification of a compound of formula(I) with a suitable chiral alcohol, separating the resultant diastereoisomeric esters by conventional means e.g. chromatography, followed by hydrolysis of the required single diastereomeric ester.

Suitable chiral alcohols for use in the process include S(+)-indanol, S(+)-methyl mandelate, S(−) methyl lactate or R(+) t-butyl lactate.

The diastereoisomeric esters of a compound of formula (I) may be prepared by conventional means such as reaction of the chiral alcohol with an activated derivative of a compound of formula (I) in an aprotic solvent such as ether e.g. tetrahydrofuran.

The activated derivative of a compound of formula(I) may be prepared from a compound of formula(I) using conventional means for preparing activated derivatives of a carboxylic acid groups such as those conveniently used in peptide synthesis.

A convenient method of preparing the diastereoisomeric esters of a compound of formula(I) is to prepare the activated derivative of a compound of formula(I) in the presence of the chiral alcohol.

Thus for example a compound of formula(I) may be treated with the Mitsunobu combination of reagents, i.e. a dialkylazo-dicarboxylate such as diethylazodicarboxylate and a triarylphosphine e.g. triphenylphosphine in the presence of the chiral alcohol.

The reaction conveniently takes place in the presence of a suitable solvent such as an ether (e.g. diethylether or tetrahydrofuran), a halohydrocarbon (e.g. diethylether or tetrahydrofuran), a halohydrocarbon (e.g. dichloromethane) or a nitrile (e.g. acetonitrile) or a mixture thereof at a temperature ranging from 0–30°.

The required single diastereoisomeric ester of a compound of formula(I) substantially free of the other diastereoisomers may be obtained from the mixture thereof by conventional means, for example by the use of conventional chromatographic procedures such as preparative hplc or by fractional crystallization.

The required enantiomer may be prepared from the corresponding single diastereoisomeric ester of a compound of formula(I) by hydrolysis e.g. alkaline hydrolysis. Thus for example the hydrolysis may be carried using an alkali metal hydroxide e.g. sodium hydroxide or lithium hydroxide in a solvent such as an ether e.g. tetrahydrofuran and water.

In any of the above reactions the carboxyl protecting group may be removed by conventional procedures known for removing such groups. Thus compounds where $R_{12}$ is a benzyl group, this may be removed by hydrolysis using an alkali metal hydroxide e.g. lithium hydroxide or sodium hydroxide in a suitable solvent such as ethanol or isopropanol, water or mixtures thereof, followed, where desired or necessary, by that addition of a suitable acid e.g. hydrochloric acid to give the corresponding free carboxylic acid.

In any of the above reactions the nitrogen protecting group may be removed by conventional procedures known for removing such groups, for example by acid or base hydrolysis. Thus when $R_{14}$ is alkoxycarbonyl e.g. t-butoxycarbonyl or phenylsulphonyl it may be removed by alkaline hydrolysis using for example lithium hydroxide in a suitable solvent such as tetrahydrofuran or an alkanol e.g. isopropanol. Alternatively the alkoxycarbonyl group may be removed by acid hydrolysis. When $R_{16}$ is t butyl group this may be removed by hydrolysis using organic acids eg formic acid.

Physiologically acceptable salts of compounds of formula (I) may be prepared by treating the corresponding acid with an appropriate base in a suitable solvent. For example alkali and alkaline metal salts may be prepared from an alkali or alkaline metal hydroxide, or the corresponding carbonate or bicarbonate thereof. Alternatively alkali or alkaline metal salts may be prepared by direct hydrolysis of carboxyl protected derivatives of compounds of formula (I) with the appropriate alkali or alkaline metal hydroxide.

Metabolically labile esters of compounds of formula (I) may be prepared by esterification of the carboxylic acid group or a salt thereof or by trans esterfication using conventional procedures. Thus, for example, acyloxyalkyl esters may be prepared by reacting the free carboxylic acid or a salt thereof with the appropriate acyloxylalkyl halide in a suitable solvent such as dimethylformamide. For the esterifcation of the free carboxyl group this reaction is preferably carried out in the presence of a quaternary ammonium halide such as tetrabutylammonium chloride or benzyltriethylammonium chloride.

Aminoalkyl esters may be prepared by transesterification of a corresponding alkyl ester e.g. methyl or ethyl ester by reaction with the corresponding aminoalkanol at an elevated temperature e.g. 50–150°.

In order that the invention may be more fully understood the following examples are given by way of illustration only.

In the Intermediates and Examples unless otherwise stated:

Melting points (m.p.) were determined on a Gallenkamp m.p. apparatus and are uncorrected. All temperatures refers to ° C. Infrared spectra were measured on a FT-IR instrument. Proton Magnetic Resonance ($^1$H-NMR) spectra were recorded at 400 MHz, chemical shifts are reported in ppm downfield (d) from Me$_4$Si, used as internal standard, and are assigned as singlets (s), doublets (d), doublets of doublets (dd), triplets (t), quartets (q) or multiplets (m). Column chromathography was carrier out over silica gel (Merck AG Darmstaadt, Germany). The following abbreviations are used in text: EA=ethyl acetate, CH=cyclohexane, DCM=dichloromethane.THF=tetrahydrofuran, Tlc refers to thin layer chromatography on silica plates. Solution were dried over anhydrous sodium sulphate; r.t. refers to room temperature.

INTERMEDIATE 1

4,6-Chloro-1-iodo-2-nitrobenzene

2-Nitro-4,6-dichloroaniline (5 g) was dissolved in a 12N solution of H$_2$SO$_4$ (20 ml) and cooled at 0°. Then, a solution of NaNO$_2$ (2.15 g) in H$_2$SO$_4$ (5 ml) was carefully added followed by polyphosphoric acid (40 ml). The reaction mixture was allowed to warm at room temperature and stirred for 3 hrs. Then, the solution was poured into crushed ice and urea was added until gas evolution ceased. The resulting mixture was treated with an aqueous solution of potassium iodide (5.6 g) and heated at 70° for 2 hrs. The reaction mixture was diluted with a 10% solution of sodium hydroxide (40 ml), extracted with ethyl acetate (3×40 ml), washed with brine (3×25 ml), dried and concentrated under vacuum. The title compound was obtained as a red oil (7.5 g).

$^1$H-NMR (CDCl$_3$): 7.67 (1H, d); 7.54 (1H, d). I.R.(nujol): 1454 cm$^{-1}$, 1350 cm$^{-1}$.

INTERMEDIATE 2

2-Iodo-3,5-dichloroaniline

To a solution of Intermediate 1 (4 g) in 95% ethanol (35 ml) glacial acetic acid (35 ml) and iron (2.8 g) was added. The reaction mixture was heated at 100° for 1 h diluted with a saturated solution of sodium hydrogen carbonate and extracted with ethyl acetate (3×20 ml). The organic layer was washed with brine (2×20 ml), dried, concentrated under vacuum to give the title compound as brown solid (2.9 g).

IR (nujol): $v_{max}$ (cm$^{-1}$)=3491 (NH2), 3103 (NH2); 1614 (C=C).

INTERMEDIATE 3

(+/−)2-(3,5-Dichloro-2-iodo-phenylamino)-pent-4-enoic Acid Benzyl Ester

To a solution of intermediate 2 (1.5 g) in dry toluene (20 ml) benzylglyoxylate (1.070 g) and Na$_2$SO$_4$ were added (2.5 g). The mixture was refluxed overnight. After filtration the resulting solution was concentrated under vacuum to a brown oil, which was then taken up with dry dichloromethane (40 ml). After cooling to −78°, TiCl$_4$ (0.57 ml) was slowly added with a syringe and stirring continued for 5 min. The solution was then allowed to warm to room temperature over 30 min by removing the dry ice/acetone bath, then cooled again to −78° and tributylallyltin (1.94 ml) added. After 1 hour the reaction was stopped by pouring it into a saturated solution of NH$_4$Cl (100 ml). The aqueous phase was extracted with ethyl acetate (2×200 ml) and the combined organic fractions washed with HCl (3N, 2×70 ml) brine (50 ml) and dried. Final purification by column chromatography (CH/EA 95/5) gave the title compound (1.05 g) as a yellow oil.

$^1$H-NMR (CDCl$_3$): 7.4–7.3 (3H, m); 6.87 (1H, d); 6.27 (1H, d); 5.72 (1H, m); 5.22–5.16 (2H, m); 5.19 (2H, s), 5.14 (1H, d); 4.16 (1H, t); 2.65 (2H, m). I.R. (neat): 3371 cm$^{-1}$; 1744 cm$^{-1}$; 1572 cm$^{-1}$.

INTERMEDIATE 4

(+/−)2-(3,5-Dichloro-2-iodo-phenylamino)-4-oxo-butyric Acid Benzyl Ester

Intermediate 3 (1.0 g) was dissolved in dry dichloromethane (40 ml) and the resulting solution cooled to −78° with a dry ice/acetone bath. Ozone was bubbled through it until a brick-red color appeared (approx 20 min), then triphenylphosphine (0.82 g) was added and the cooling bath removed. After the warm-up was complete the solution was concentrated to dryness and then purified by column chromatography (CH/EA 80/20) to give the title compound (0.745 g) as a colorless oil.

$^1$H-NMR (CDCl$_3$): 9.77 (1H, s); 7.36–7.28 (5H, m); 6.91 (1H, d); 6.40 (1H, d); 5.34 (1H, d); 5.20 (2H, s); 4.50 (1H, dt); 3.09 (2H, d). I.R. (nujol). 3371 cm$^{-1}$1738 cm$^{-1}$, 1732 cm$^{-1}$.

INTERMEDIATE 5

(+/−)(E)-2-(3,5-Dichloro-2-iodo-phenylamino)-hex-2-endioic Acid-6-benzyl-1-tert-butylester Intermediate 4 (8.2 g) was dissolved in dry toluene (200 ml), (tert-butoxycarbonyl methylene) triphenylphosphorane was then added and the mixture was stirred at 100° C. for 2 h. The solvent was removed under vacuum and the crude product was purified by flash-chromatography (CH/EA 95/5) to give the title compound (6.00 g) as a white solid. m.p. 95–96°.

$^1$H-NMR (d$_6$-acetone): 7.4–7.3 (m, 5H); 6.92 (d, 1H); 6.82 (dt, 1H); 6.67 (d, 1H); 5.88 (dt, 1H); 5.40 (d, 1H); 5.24 (s, 2H); 4.66 (dt, 1H); 3.0–2.8 (m, 2H); 1.5 (s, 9H).

INTERMEDIATE 6

(+/−)(E)-5-(3,5-Dichloro-2-iodo-phenylamino)-hex-2-endioic Acid 6-Benzyl Ester

Intermediate 5 (0.2 g) was dissolved in formic acid (5 ml) and stirred at room temperature for 24 h. The reaction mixture was then evaporated to dryness to give the title compound (0.180 g).

$^1$H NMR (DMSO): 12.3 (bs, 1H); 7.4–7.3 (m, 5H); 7.01 (d, 1H); 6.73 (dt, 1H); 6.66 (d, 1H); 5.87 (d, 1H); 5.37 (d, 1H); 5.18 (s, 2H); 4.73 (dt, 1H); 2.81 (t, 1H).

INTERMEDIATE 7

(+/−)-(E,E)-5-[4-(2-Cyano-vinyl)-phenylcarbamoyl]-2-(3,5-dichloro-2-iodo-phenylamino)-penten-4-enoic Acid Benzyl Ester Intermediate 6 (0.2 g) was dissolved in dry THF (3 ml) at −20° and PCl$_5$ (0.1 g) was added portionwise. The mixture was stirred for 1 h at −20°, then pyridine (0.046 ml) and 3-(4-amino-phenyl)-acrylamide (0.074 g) were added. The temperature was allowed to increase slowly to room temperature over 2 h. After an additional 2 h, the solution was taken up with ethyl acetate, washed twice with 3N HCl, then with water and brine. After drying and filtration the solution was concentrated to give a crude product, which was purified by column chromatography (CH/EA 7/3) to give the title compound (0.09 g) as an 8/2 mixture with a non-identifiable isomer at one of the two double bonds. mp: 132–134° C.

NMR: $^1$H d (CDCl$_3$) 9.46 (1H, bs), 7.79 (2H, d), 7.62 (2H, d), 7.50 (1H, d), 7.5–7.3 (5H, m), 7.0–6.9 (2H, m), 6.67 (1H, d), 6.25 (1H, d), 6.17 (1H, d), 5.43 (1H, d), 5.26 (2H, s), 4.69 (1H, m), 2.93 (2H, m). IR: (CDCl$_3$) Vmax (cm$^{-1}$) 2210, 1738.

INTERMEDIATE 8

(+/−)(E)-5,7-Dichloro-4-tert-butoxycarbonylmethylene-1,2,3,4-tetrahydro-guinoline-2-carboxylic Acid Benzyl Ester Intermediate 5 (6.5 g) was dissolved in dry dimethylformamide (150 ml). To this solution, tetrakis (triphenylphosphine)palladium (0.65 g) and triethylamine (9.15 ml) were added and the reaction mixture was heated to 100° for 1 h under nitrogen atmosphere. The reaction mixture was then cooled to room temperature, diluted with ethyl acetate (250 ml), washed with a saturated solution of aqueous NH$_4$Cl (100 ml) and with brine (3×100 ml). The organic layer was separated, dried, filtered and evaporated under vacuum. The crude product was purified by flash chromatography (EA/CH 1/9) to give the title compound (4 g) as a white solid.

$^1$H-NMR (DMSO): 7.44–7.3 (m, 5H); 6.77 (d, 1H); 6.70 (d, 1H); 6.47 (bs, 1H); 6.45 (s, 1H); 5.21 (d, 1H); 5.02 (d, 1H); 4.40 (td 1H); 3.98 (dd, 1H); 3.11 (ddd, 1H); 1.5 (s, 9H).

INTERMEDIATE 9

(+/−)(E)-5,7-Dichloro-4-carboxymethylene-1,2,3,4-tetrahydro-quinoline-2-carboxylic Acid Benzyl Ester Intermediate 8 (0.96 g) was suspended in formic acid (40 ml) and stirred at room temperature for 2 hours. The solvent was removed under vacuum, then the solid was suspended in ether and then concentrated again to dryness to give the title compound (0.86 mg) as a white solid. m.p. 210–212°.

$^1$H-NMR (d$_6$-acetone): 11.2–10.6 (bs, 1H); 7.4–7.3 (m, 5H); 6.78 (d, 1H); 6.71 (d, 1H); 6.57 (s, 1H); 6.49 (bs, 1H); 5.18 (d, 1H), 5.03 (d, 1H); 4.41 (t, 1H); 4.05–4 (m, 1H); 3.14 (ddd, 1H); I.R.(Nujol): 3373 cm$^{-1}$; 1726 cm$^{-1}$; 1688 cm$^{-1}$; 1614 cm$^{-1}$.

INTERMEDIATE 10

(+/−)(E)-5,7-Dichloro-4-[2-(pyridyl)thiocarbonylmethylene]-1,2,3,4-tetrahydro-quinoline-2-carboxylic Acid Benzyl Ester Intermediate 9 (3.7 g) was dissolved in dry tetrahydrofuran (50 ml). To this solution, triphenylphosphine (6.17 g) and 2,2'-dithiopyridine (5.2 g) were added and the reaction mixture was stirred for 1 h at room temperature under nitrogen atmosphere. The reaction mixture was diluted with ethyl acetate (200 ml), then washed with HCl 1N (50 ml), NaOH 2M (50 ml) and brine (2×50 ml). The organic layer was separated, dried, filtered and evaporated under vacuum. The crude product was purified by flash chromatography (EA/CH 3/7) to give the title compound (3.5 g) as a yellow foam.

$^1$H -NMR (DMSO): 8.59 (m, 1H); 7.78 (dt, 1H); 7.62 (m, 2H); 7.45–7.27 (m, 5H); 6.84–6.76 (s, 3H); 5.15 (d, 1H); 4.97 (d, 1H); 4.40 (m, 1H); 3.92 (dd, 1H); 2.80 (m, 1H).

INTERMEDIATE 11

(+/−)-(E,E)-5,7-Dichloro-4-[4-(2-cyano-vinyl)-phenylcarbamoylmethylene]-1,2,3,4-terahydro-guinoline-2-carboxylic Acid Benzyl Ester Intermediate 7 (0.08 g) was dissolved in acetonitrile (3 ml) and the solution deoxygenated with a flow of dry nitrogen for 5 min. Tetrakis (triphenylphosphine)palladium (0.021 g) was added and the heterogeneous mixture heated to 80°. After 3 h the mixture was cooled, diluted with ethyl acetate and washed twice with 3N HCl, then with water and brine. After drying and filtration the solution was concentrated to give a crude product, which was purified by column chromatography (CH/EA 7.5/2.5) to give the title compound (0.04 g) as a white solid. mp: 146–148° C.

NMR: $^1$H d (CDCl$_3$) 10.42 (1H, bs), 7.71 (2H, d), 7.60 (2H, d), 7.57 (1H, d), 7.27 (1H, d), 7.23 (6H, m), 6.7 (2H, m), 6.32 (1H, d), 5.04 (1H, d), 4.86 (1H, d), 4.38 (1H, m), 4.24 (1H, dd) 2.81 (1H, dd). IR: (CDCl$_3$) Vmax (cm$^{-1}$) 3375, 3325, 2216, 1730, 1717, 1616, 1589.

INTERMEDIATE 12

(+/−)(E,E)-4-[4-(2-tert-Butoxycarbonyl-vinyl)-phenylcarbamoylmethylene]-5,7-dichloro-1,2,3,4-tetrahydro-quinoline-2-carboxylic Acid Benzyl Ester Intermediate 9 (0.10 g) was dissolved in dry tetrahydrofuran (8.5 ml) and the solution was cooled to −20°. At the same temperature PCl$_5$ (0.066 g) was added and the reaction mixture was warmed to 0° and stirred for 1 h under nitrogen atmosphere. Pyridine (0.031 ml) and 4-(4-nitro-phenyl)-but-3-enoic acid t-butyl ester (0.061 g) were then added and the reaction mixture was stirred for 1 h at room temperature. The reaction mixture was then diluted with a saturated solution of NH$_4$Cl (5 ml) and extracted with ethyl acetate (50 ml), then the organic phase was washed with HCl 1 N (50 ml), and with brine (50 ml). The organic layer was separated, dried, filtered and evaporated under vacuum to give a crude product which was purified by flash chromatography (EA/CH 8:2) to give the title compound (0.10 g) as a yellow solid mp 85°.

$^1$H NMR (DMSO): 10.34 (s, 1H); 7.69 (d 2H); 7.49 (d, 2H); 7.48 (bs, 1H); 7.34 (d, 1H); 7.27 (d, 1H); 7.23 (m, 5H); 7.03 (bs, 1H); 6.73–6.71 (m, 3H); 6.50 (d, 1H); 5.05 (d, 1H); 4.85 (d, 1H); 4.4 (m, 1H); 4.25 (m, 1H); 2.80 (m, 1H).

INTERMEDIATE 13

(+/−)(E,E)-4-[4-(2-Carbamoyl-vinyl)-phenylcarbamoylmethylene]-5,7-dichloro-1,2,3,4-tetrahydro-quinoline-2-carboxylic Acid Benzyl Ester Intermediate 10 (0.3 g) was dissolved in dry tetrahydrofuran (16 ml). To this solution, 4-(4-amino-phenyl)but-3-enoic acid amide (0.029 g) was added and the reaction mixture was refluxed for 36 h. The reaction mixture was diluted with ethyl acetate (8 ml), then washed with HCl 3N (10 ml), NaOH 5% (10 ml) and brine (10 ml). The organic layer was separated, dried, filtered and evaporated under vacuum. The crude product was purified by flash chromatography (EA) to give the title compound (0.035 g) as a yellow solid m.p. >250°.

$^1$H NMR (DMSO): 10.12 (s, 1H), 7.55 (d, 2H); 7.24 (m, 5H); 7.10 (d, 2H); 6.85 (t, 1H); 6.70 (m, 3H); 5.04–4.84 (d, d, 2H); 4.35 (m, 1H); 4.25 (m, 1H); 3.10 (m, 2H); 2.79 (m, 1H); 2.62 (t, 2H); 1.34 (s, 9H). IR (nujol): 3368, 3298, 1700, 1686.

INTERMEDIATE 14

(+/−)(E)-5,7-Dichloro-4-[4-(2-morpholin-4-yl-ethoxy)-phenylcarbamoylmethylene-]-1,2,3,4-tetrahydro-quinoline-2-carboxylic Acid Benzyl Ester Intermediate 10 (0.097 g) was dissolved in dry toluene (10 ml). To this solution, 4-[2-(4-morpholinyl)ethoxy]-benzeneamine (0.053 g) was added and the reaction mixture was refluxed for 1 h. The reaction mixture was then cooled and a precipitate was formed which was filtered and triturated with isopropanol to give the title compound (0.075 g) as a white solid.

$^1$H NMR (DMSO): 10.05 (s, 1H); 7.56 (d, 2H); 7.25 (m, 6H); 6.87 (d, 2H); 6.71 (d, 1H); 6.70 (d, 1H); 6.68 (s, 1H); 5.05 (d, 1H); 4.85 (d, 1H); 4.35 (m, 1H); 4.24 (dd, 1H); 4.03 (t, 2H); 3.57 (t, 4H); 2.8 (dd, 1H); 2.65 (t, 2H); 2.43 (m, 4H). IR (nujol): 3335, 1722, 1643.

INTERMEDIATE 15

N-[2-(4-Nitro-phenoxy)ethyl]-isobutyramide 2-(4-Nitro-phenoxy)ethylamine (0.27 g) was dissolved in dry DCM (8.5 ml) and dry pyridine (0.15 ml) and isobutyryl chloride (0.12 ml) were then added. After stirring for 1 h at room temperature, the reaction mixture was then diluted with HCl 3 N (50 ml) and extracted with ethyl acetate (50 ml), then the organic phase was washed with brine (50 ml). The organic layer was separated, dried, filtered and evaporated under vacuum to give a crude product which was crystallized (diethyl ether, 7 ml) to give the title compound (0.11 g) as a yellow solid. m.p. 102–103°.

$^1$H NMR (CDCl$_3$): 8.22 (d, 2H); 6.98 (d, 2H); 5.88 (bs, 1H); 4.15 (t, 2H); 3.72 (m, 2H); 2.39 (m, 1H); 1.18 (d, 6H); IR (nujol): 3319, 1647, 1593, 1340, 1175.

INTERMEDIATE 16

N-[2-(4-Amino-phenoxy)-ethyl]-isobutyramide

Intermediate 15 (0.19 g) was dissolved in methanol (5 ml) and Pd on carbon 5% (0.19 g) was then added. After stirring for 1 h 30 min at room temperature under hydrogen (1 atm), the reaction mixture was filtered on Celite and evaporated under vacuum to give the title compound (0.15 g) as a orange solid m.p. 99–100°.

$^1$H NMR (CDCl$_3$): 6.73 (m, 2H); 6.65 (m, 2H); 5.92 (bs, 1H); 3.96 (t, 2H); 3.62 (m, 2H); 3.46 (bs, 2H); 2.37 (m, 1H); 1.15 (d, 6H); IR (nujol): 3300, 1663.

INTERMEDIATE 17

(+/−)(E)-5,7-Dichloro-4-[4-(2-isobutyrylamino-ethoxy)-phenylcarbamoylmethylene]-1,2,3,4-tetrahydro-quinoline-2-carboxlic Acid Benzyl Ester Intermediate 10 (0.078 g) was dissolved in dry toluene (8 ml). To this solution, intermediate 16 (0.044 g) was added and the reaction mixture was refluxed for 45 min. The reaction mixture was then cooled and a precipitate was formed which was filtered and triturated with isopropanol to give the title compound (0.080 g) as a white solid.

$^1$H NMR (DMSO): 10.06 (s, 1H); 7.95 (t, 1H); 7.56 (d, 2H); 7.26–7.2 (m, 6H); 6.87 (d, 2H); 6.71 (d, 1H); 6.69 (d, 1H); 6.68 (s, 1H); 5.05 (d, 1H); 4.84 (d, 1H); 4.35 (m, 1H); 4.24 (dd, 1H); 3.92 (t, 2H); 3.36 (m, 2H); 2.80 (dd, 1H); 2.36 (m, 1H); 0.97 (d, 6H). IR (nujol): 3315, 3292, 1722. 1649.

INTERMEDIATE 18

N-(4-t-Butoxycarbonylamino-phenyl)-2-methoxy-acetamide

To a stirred solution of N-t-butoxycarbonyl-1,4-phenylene diamine (0.25 g) in dry tetrahydrofuran (20 ml) were added pyridine (0.12 ml) and methoxyacetyl chloride (0.15 g) and the reaction mixture was stirred for 1 hrs. The solution was diluted with ethyl acetate (50 ml), washed with a 3N solution of hydrochloric acid (30 ml) and brine (30 ml), dried and concentrated in vacuum to give the title compound (0.35 g). T.l.c. CH/EA acetate 1/1. R$_f$=0.33.

1H-NMR (CDCl$_3$): 8.18 (bs, 1H), 7.50 (d, 2H), 7.32 (d, 2H), 6.44 (bs, 1H), 4.00 (s, 2H), 3.49 (s, 3H), 1.51 (s, 9H).

INTERMEDIATE 19

N-(4-Amino-phenyl)-2-methoxy-acetamide

A solution of intermediate 18 (0.35 g) in dichloromethane/trifluoroacetic acid (10 ml/10 ml) was stirred for 2 hrs. The solvent was evaporated, the crude product was diluted with a 2N solution of sodium hydroxyde and extracted with ethyl acetate (4×50 ml) and dichloromethane (50 ml). The collected organic layers were dried and concentrated in vacuum. The crude product was purified by silica gel column chromatography using ethyl acetate as eluant to give the title compound (0.16 g). T.l.c. ethyl acetate, R$_f$=0.43.

1H-NMR (CDCl$_3$): 8.05 (bs, 1H), 7.33 (d, 2H), 6.66 (d, 2H), 3.99 (s, 2H), 3.60 (bs, 2H), 3.49 (s, 3H).

INTERMEDIATE 20

(+/−)(E)-5,7-Dichloro-4-[4-(2-methoxy-acetylamino)-phenylcarbamoylmethylene]-1,2,3,4-tetrahydro-quinoline-2-carboxylic Acid, Benzyl Ester To a stirred solution of intermediate 10 (0.12 g) in dry toluene (10 ml) was added intermediate 19 (0.053 g) and the reaction mixture was heated at reflux for 2 hrs. The reaction mixture was cooled at 24°, affording a precipitate which was filtered to obtain the pure title compound (0.118 g). T.l.c. ethyl acetate, R$_f$=0.75.

1H-NMR (DMSO): 10.15 (bs, 1H), 9.64 (bs, 1H), 7.58 (m, 4H), 7.25 (m, 6H), 6.72–6.70 (m, 3H), 5.06 (d, 1H), 4.85 (d, 1H), 4.35 (m, 1H), 4.25 (dd, 1H), 3.96 (s, 2H), 3.35 (s, 3H), 2.81 (dd, 1H).

INTERMEDIATE 21

N-4-(tert-Butoxycarbonylamino-phenyl)-2-benzyloxycarbonylamino-acetamide

To a solution of carbobenzyloxyglycine (0.6 g) in acetonitrile (40 ml) was added 1-hydroxybenzotriazole 90.4 g), 1-(3-dimethylaminopropyl)-3-ethylcarbodiimide hydrochloride (1.1 g) and 4-(tert-butoxycarbonylamino) aniline (0.5 g) and the reaction mixture was stirred at reflux for 5 hrs. After dilution with ethyl acetate, the solution was washed with 3 N hydrochloric acid, brine, 5% solution of sodium hydroxide and brine. The organic layer was dried, filtered and evaporated under vacuum to give a crude product which was triturated in diethyl ether (5 ml) to give the title compound (0.54 g) as a pale brown solid.

$^1$H NMR (CDCl$_3$): 7.79 (bs, 1H); 7.45–7.3 (m, 9H); 6.44 (bs, 1H); 5.43 (bs, 1H); 5.17 (s, 2H); 3.98 (d, 2H); 1.51 (s, 9H); IR (nujol): 3439, 1724.

INTERMEDIATE 22

N-4(tert-Butoxycarbonylamino-phenyl)-2-amino-acetamide

A suspension of intermediate 21 (0.53 g) in methanol (25 ml) was hydrogenated at 1 atm for 1 hrs in the presence of 5% Pd/C (0.25 g) as catalyst. The catalyst was filtered off on a paid of celite and the solution was evaporated to obtain the title compound (0.32 g) as a pale pink solid.

$^1$H NMR (DMSO): 9.7 (bs, 1H); 9.22 (bs, 1H); 7.48 (d, 2H); 7.34 (d, 2H); 3.20 (s, 2H); 2.00 (b, 2H); 1.45 (s, 9H); IR (nujol): 3314, 1732, 1645, 1603.

INTERMEDIATE 23

N-4(tert-Butoxycarbonylamino-phenylcarbamoylmethyl)-isobutyramide

To a solution of intermediate 22 (0.32 g) in THF (25 ml) was added pyridine (0.19 ml) and butyryl chloride (0.15 ml) and the reaction mixture was stirred for 1 hrs. After dilution with ethyl acetate, the solution was washed with 3 N hydrochloric acid. The organic layer was dried, filtered and evaporated under vacuum to give a crude product which was triturated in diethyl ether (5 ml) to give the title compound (0.31 g) as a white solid.

$^1$H NMR (DMSO): 9.80 (s, 1H); 9.22 (s, 1H); 8.00 (t, 1H); 7.43 (d, 2H); 7.34 (d, 2H); 3.81 (d, 2H); 2.44 (m, 1H); 1.45 (s, 9H); 1.01 (d, 6H); IR (nujol): 1724, 1705, 1634.

INTERMEDIATE 24

N-4(-Amino-phenylcarbamoylmethyl)-isobutyramide

A solution of intermediate 23 (0.31 g) in dichloromethane/trifluoroacetic acid (6 ml/6 ml) was stirred for 1 hrs. The solution was evaporated and the residue was diluted with 5% solution of NaOH and extracted with ethyl acetate (4×50 ml). The organic layer was dried, filtered and evaporated under vacuum to give a crude product which was purified by flash chromathography using ethyl acetate as to give the title compound (0.16 g) as a brown foam.

$^1$H NMR (DMSO): 9.47 (s, 1H); 7.96 (t, 1H); 7.18 (d, 2H); 6.48 (d, 2H); 4.83 (bs, 2H); 3.77 (d, 2H); 2.44 (m, 1H); 1.00 (d, 6H); IR (nujol): 3306, 1678, 1651.

INTERMEDIATE 25

(+/−)(E)-5,7-Dichloro-4-(4-isobutyrrylaminomethylcarbonylamino-phenylcarbamoylmethylene)-1,2,3,4-tetrahydro-quinoline-2-carboxylic Acid Benzyl Ester Intermediate 10 (0.53 g) was dissolved in toluene (50 ml). To this solution intermediate 24 (0.31 g) was added and the reaction mixture was stirred for 2 h at 110°. The precipitated white solid was filtered and washed with ethyl ether (30 ml) to give the title compound (0.58 g) as a white solid.

$^1$H NMR (DMSO): 10.14 (s, 1H); 9.90 (s, 1H); 8.04 (t, 1H); 7.58 (d, 2H); 7.49 (d, 2H); 7.25 (m, 5H); 6.72 (d, 1H); 6.70 (d, 1H); 6.70 (s, 1H); 5.05 (d, 1H); 4.86 (d, 1H); 4.36 (m, 1H); 4.25 (dd, 1H); 3.83 (d, 2H); 2.82 (dd, 1H); 2.46 (m, 1H); 1.01 (d, 6H). IR (nujol): 1717, 1643, 3281.

EXAMPLE 1

(+/−)-(E,E)-5,7-Dichloro-4-[4-(2-cyano-vinyl)-phenylcarbamoylmethylene]-1,2,3,4-terahydro-quinoline-2-carboxylic Acid Intermediate 11 (0.032 g) was dissolved in 95% ethanol (4 ml) and water (1 ml) and treated at room temperature for 1 h with LiOH (0.005 g). The solution was then concentrated and the resulting solid was triturated with 3N HCl (2 ml) for 1 h. Filtration of the suspension yielded the title compound (0.025 g) as a yellow solid mp: >200°.

NMR: $^1$H d (CDCl$_3$) 12.73 (1H, bs), 10.39 (1H, bs), 7.70 (2H, d), 7.60 (2H, d), 7.56 (1H, d), 7.22 (1H, s), 7.15 (1H, d), 6.70 (1H, d), 6.68 (1H, d), 6.31 (1H, d), 4.13 (1H, td), 3.90 (1H, dd), 3.03 (1H, dd). IR: (CDCl$_3$) Vmax (cm$^{-1}$) 3321, 2286, 1770, 1690.

EXAMPLE 2

(+/−)(E,E)-4-[4-(2-tert-Butoxycarbonyl-vinyl)-phenylcarbamoylmethylene]-1,2,3,4-tetrahydro-quinoline-2-carboxylic Acid Intermediate 12 (0.046 g) was suspended in ethanol (5 ml) and water (2 ml). To this solution LiOH(H$_2$O) (0.007 g) was added and the reaction mixture was stirred for 0.5 h at room temperature until a clear pale yellow solution was obtained. HCl 2 N (5 ml) was then added dropwise and the resulting acidic solution diluted with ethyl acetate (10 ml); The organic layer was separated, dried and evaporated under vacuum. The crude product was triturated with diethyl ether (3 ml) and petrolium ether (3 ml). The precipitate was filtered, washed with small amounts of petrolium ether and dried to give the title compound (0.015 g) as a yellow solid m.p. 140°.

$^1$H NMR (DMSO): 12.84 (bs, 1H); 10.40 (bs, 1H); 7.68 (d, 2H); 7.62 (d, 2H); 7.61 (d, 1H); 7.15 (bs, 1H); 6.70 (m, 3H); 6.40 (d, 1H); 4.13 (m, 1H); 3.94 (dd, 1H); 3.01 (dd, 1H); 1.47 (d, 9H).

EXAMPLE 3

(+/−(E,E)-4-[4-(2-Carbamoyl-vinyl)-phenylcarbamoylmethylene]-5,7-dichloro-1,2,3,4-tetrahydro-quinoline-2-carboxylic Acid Intermediate 13 (0.0989) was suspended in ethanol (5 ml) and water (2.5 ml). To this solution LiOH.(H$_2$O) (0.006 g) was added and the reaction mixture was stirred for 2 h at room temperature until a clear pale yellow solution was obtained. HCl 2 N (5 ml) was then added dropwise and the resulting acidic solution diluted with water (10 ml); the precipitate thus formed was filtered, washed with small amounts of cold water and dried to give the title compound (0.020 g) as a white solid m.p >250°.

$^1$H NMR (DMSO): 12.71 (bs, 1H); 10.30 (bs, 1H); 7.67 (d, 2H); 7.49 (d, 2H); 7.46 (bs, 1H); 7.01 (bs, 1H); 7.34 (d, 1H); 7.14 (db, 1H); 6.70 (m, 1H); 6.69 (d, 1H); 6.68 (d, 1H) 4.12 (m, 1H); 3.90 (dd, 1H); 3.03 (dd, 1H) m.p >250°. IR (nujol): 3310, 3420, 1710, 1657, 1610.

EXAMPLE 4

(+/−)(E)-5,7-Dichloro-4-[4-(2-morpholin-4-yl-ethoxy)-phenylcarbamoylmethylene]-1,2,3,4-tetrahydro-guinoline-2-carboxylic Acid Intermediate 14 (0.049 g) was suspended in ethanol (9 ml) and water (3 ml). To this solution LiOH(H$_2$O) (0.014 g) was added and the reaction mixture was stirred for 0.5 h at room temperature until a clear pale yellow solution was obtained. HCl 3 N (5 ml) was then added dropwise until pH=3 and the resulting acidic solution diluted with ethyl acetate (50 ml) and water (50 ml); The organic layer was separated, dried and evaporated under vacuum. The crude product was triturated with water (2 ml) and with diethyl ether/EA (1/1) to give the title compound (0.027 g) as a yellow solid.

¹H NMR (DMSO): 12.67 (bs, 1H); 10.10 (s, 1H); 7.55 (d, 2H); 7.13 (d, 1H); 6.87 (d, 5 2H); 6.70 (d, 1H); 6.67 (s, 1H); 6.65 (d, 1H); 4.10–4.04 (m, 3H); 3.85 (m, 1); 3.57 (m, 4H); 3.05 (dd, 1H); 2.6 (m, 2H); 2.4 (m, 4H). IR (nujol): 3387.

EXAMPLE 5

(+/−)(E)-5,7-Dichloro-4-(4-cyanomethyl-phenylcarbamoylmethylene)-1,2,3,4-tetrahydro-quinoline-2-carboxylic Acid 4-Cyanomethylaniline (0.081 g), was added to a solution of intermediate 10 (0.2 g) dissolved in dry toluene (10 ml) and dry tetrahydrofuran (10 ml). The reaction mixture was stirred for 3 h at 110° and then diluted with ethyl acetate (50 ml), washed with a saturated aqueous solution of $NH_4Cl$ (50 ml) and with brine (50 ml). The organic layer was separated, dried, filtered and evaporated under vacuum to give a crude product which was triturated in ethyl acetate (5 ml) and petroleum ether (20 ml). The yellow solid thus obtained (0.140 g), was dissolved in ethanol (20 ml) and water (5 ml). To this solution, $LiOH(H_2O)$ (0.023 g) was added and the reaction mixture was stirred for 1 h at room temperature. HCl 2 N (5 ml) was then added dropwise and the resulting acidic solution diluted with water (30 ml); the precipitate thus formed was filtered, washed with small amounts of cold water and dried to give the title compound (0.057 g) as a yellow solid m.p.: 200–202°.

¹H (DMSO): 12.7 (bs, 1H); 10.2 (s, 1H); 7.65 (d, 2H); 7.27 (d, 2H); 6.7–6.67 (m, 3H); 4.11 (m, 1H); 3.96 (s, 2H); 3.89 (dd, 1H); 3.05 (dd, 1H). IR (nujol): 3366; 3321; 2270; 1728.

EXAMPLE 6

(+/−)(E)-5,7-Dichloro-4-[4-(2-isobutyrylamino-ethoxy)-phenylcarbamoylmethylene]-1,2,3,4-tetrahydro-guinoline-2-carboxylic Acid Intermediate 17 (0.066 g) was suspended in ethanol (9 ml) and water (3 ml). To this solution $LiOH.(H_2O)$ (0.019 g) was added and the reaction mixture was stirred for 1 h at room temperature until a clear pale yellow solution was obtained. After evaporation of the solvent, HCl 1 N was then added dropwise until pH=1 and the resulting acidic solution diluted with water (30 ml); the precipitate thus formed was filtered, washed with small amounts of cold water, triturated with isopropanol (2 ml) and dried to give the title compound (0.029 g) as a white solid.

¹H NMR (DMSO): 12.70 (s, 1H); 10.01 (s, 1H); 7.95 (t, 1H); 7.54 (d, 2H); 7.10 (d, 1H); 6.87 (d, 2H); 6.69 (d, 1H); 6.67 (d, 1H); 6.66 (bs, 1H); 4.10 (m, 1H); 3.92 (t, 2); 3.88 (dd, 1H); 3.36 (m, 2H); 3.05 (dd, 1H); 2.36 (m, 1H); 0.97 (d, 6H). IR (nujol): 3333, 1726, 1650, 1628.

EXAMPLE 7

(+/−)(E)-5,7-Dichloro-4-[4-(2-methoxy-acetylamino)-phenylcarbamoylmethylene-1,2,3,4-tetrahydro-quinoline-2-carboxylic Acid To a stirred solution of intermediate 20 (0.06 g) in ethanol/water (6 ml/2 ml), was added lithium hydroxide monohydrate (0.018 g) and the reaction mixture was stirred for 1 hrs. The solution was evaporated, then diluted with a 3N solution of hydrochloric acid (5 ml). The formed precipitate was filtered, washed with water and triturated in acetonitrile (2 ml) to give the title compound (0.034 g).

1H-NMR (DMSO): 12.72 (s, 1H), 10.11 (s, 1H), 9.68 (s, 1H), 7.57 (m, 4H), 7.11 (d, 1H), 6.69 (d, 1H), 6.68 (s, 1H), 6.67 (d, 1H), 4.11 (m, 1H), 3.96 (s, 2H), 3.9 (dd, 1), 3.36 (s, 3H), 3.06 (dd, 1H).

EXAMPLE 8

(+/−)(E)E-5,7-Dichloro-4-[4-(2-cyano-vinyl) phenylcarbamoylmethylene]-1,2,3,4-tetrahydro-quinoline-2-carboxylic Acid Sodium Salt Example 1 (0.040 g) was suspended in water (5 ml) and methanol (1 ml). NaOH 1 M (0.093 ml) was then added and the reaction mixture was stirred for 10' at room temperature until a clear pale yellow solution was obtained. The resulting solution was then freeze-dried for 32 h to give the title compound (0.033 g) as a yellow solid.

¹H NMR (DMSO); 11.86 (bs, 1H); 7.60 (d, 2H); 7.55 (d, 1H); 7.32 (d, 2H); 6.78 (d, 1H); 6.74 (d, 1H); 6.54 (m, 1H); 6.50 (d, 1H); 6.32 (d, 1H); 3.52 (m, 1H); 3.16 (m, 1H); 2.73 (m, 1H). IR (nujol): 3326–2670, 2218, 1664, 1600.

EXAMPLE 9

(+/−)(E)-5,7-Dichloro-4-(4-isobutyrylaminomethylcarbonylamino-phenylcarbamoylmethylene)-1,2,3,4-tetrahydro-quinoline-2-carboxylic Acid Sodium Salt Intermediate 25 (0.58 g) was suspended in ethanol/methanol solution (95:5 respectively) (0.81 ml). NaOH 1N (0.93 ml) was added and the solution was stirred 1 h at RT. The solution becomes clear yellow. Ethyl acetate (100 ml) and diethyl ether (50 ml) were in turn added dropwise and the precipitated yellow solid filtered and dried to give the title compound (0.44 g) as a yellow solid.

¹H NMR (DMSO): 11.19 (bs, 1H); 9.99 (bs, 1H); 8.17 (t, 1H); 7.66 (m, 2H); 7.50 (m, 2H); 6.75–6.69 (d+bs, 2H); 6.53–6.50 (s+d, 2H); 3.83 (d, 2H); 3.50–3.41 (m+dd, 2H); 2.58–2.45 (dd+m, 2H); 1.01 (d, 6H). IR (nujol): 3294, 1691, 1653.

PHARMACY EXAMPLE

|  | % w/v |
|---|---|
| Intravenous Infusion | |
| A glycine antagonist of formula (I) | 0.3–0.5 |
| Polysorbate 80 | 1 |
| tris(hydroxymethyl)aminomethane | 0.54 |
| Dextrose solution 5% w/v | qs to volume |
| Intravenous injection | |
| A glycine antagonist of formula (I) | 0.3–3 |
| Polysorbate 80 | 1 |
| tris(hydroxymethyl)aminomethane | 0.54 |
| Dextrose solution 5% w/v | qs to volume |

The glycine antagonist and Polysorbate were added to a solution of tris(hydromethyl)aminomethane in a 5% aqueous dextrose solution suitable for injection. The solution was filtered through a sterile 0.2 micron sterlising filter and filled in containers before being sterilised by autoclaving.

The affinity of a compound of the invention for strychnine insensitive glycine binding site located on the NMDA receptor complex was determined using the procedure of Kishimoto H. et al J. Neurochem 1981, 37, 1015–1024. The pKi values obtained with representative compounds of the invention are given in the following table.

| Example No. | pKi |
| --- | --- |
| 3 | 8.1 |
| 4 | 7.2 |
| 5 | 8.1 |
| 6 | 7.8 |
| 7 | 8.2 |
| 9 | 8.1 |

The ability of compounds of the invention to inhibit NMDA induced convulsions in the mouse was determined using the procedure of Chiamulera C et al. Psychopharmacology 1990, 102, 551–552. In this test the ability of the compound when administered iv to inhibit the generalized seizures induced by an intracerebroventicular injection of NMDA in mice was examined at 0.1 mg/kgdose.

The results as percent (%) of inhibition at 0.1 mg/kg dose for representative compounds are given below:

| Ex No. | % of inhibition |
| --- | --- |
| 7 | 40% |
| 9 | 40% |
| 6 | 40% |
| 3 | 40% |

No untoward effects have been observed when compounds of the invention have been administered to mice (either i.v. or po) at pharmacologically active doses.

What is claimed is:

1. A compound of formula (I)

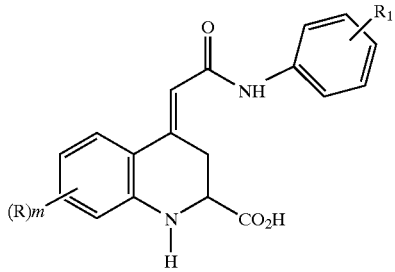

(I)

a salt, or a metabolically labile ester thereof wherein R represents a group selected from halogen, alkyl, alkoxy, amino, alkylamino, dialkylamino, hydroxy, trifluoromethyl, trifluoromethoxy, nitro, cyano, $SO_2R_2$ or $COR_2$ wherein $R_2$ represents hydroxy, methoxy, amino, alkylamino or dialkylamino: m is zero or an integer 1 or 2;

$R_1$ represents a group $(CH_2)nCN$, $—CH=CHR_3$, $(CH_2)nNHCOCH_2R_4$ or $O(CH_2)pNR_5R_6$; $R_3$ represents cyano or the group $COR_7$;

$R_4$ represents alkoxy or a group $NHCOR_8$;

$R_5$ and $R_6$ each represent independently hydrogen or alkyl, or $R_5$ and $R_6$ together with the nitrogen atom to which they are attached represent a heterocyclic group, or $R_5$ is hydrogen and $R_6$ is the group $COR_9$;

$R_7$ represents an alkoxy, amino or hydroxyl group;

$R_8$ represents a hydrogen atom or optionally substituted alkyl, alkoxy, phenyl, heteroaryl or heterocyclic group;

$R_9$ is the group $R_8$ or the group $NR_{10}R_{11}$ wherein $R_{10}$ represents hydrogen or alkyl group;

$R_{11}$ represents optionally substituted alkyl, phenyl, heteroaryl, heterocyclic or cycloalkyl group;

n is zero or an integer from 1 to 4; p is an integer from 2 to 4.

2. A compound of formula(I) as claimed in claim 1, a physiologically acceptable salt or a metabolically labile ester thereof.

3. A compound of formula(I) as claimed in claim 1 wherein m is 1 or 2, and R is halogen atom in the 5 and/or 7 position.

4. A compound of formula(I) as claimed in claim 1 wherein m is 2 and R is chlorine in the 5 and 7 position.

5. A compound of formula(I) as claimed in claim 1 wherein $R_1$ is the group $(CH_2)nCN$, $—CH=CHR_3$, (wherein $R_3$ is cyano or $COR_7$, in which $R_7$ is $C_{1-4}$ alkoxy or amino), $(CH_2)nNHCOCH_2R_4$ (wherein $R_4$ is $C_{1-4}$ alkoxy or $NHCOR_8$ wherein $R_8$ is hydrogen or $C_{1-4}$alkyl), $O(CH_2)pNR_5R_6$ (wherein $R_5$ and $R_6$ are hydrogen or $NR_5R_6$ represents morpholino or $R_5$ represents hydrogen and $R_6$ is $COR_9$ wherein $R_9$ is hydrogen or $C_{1-4}$alkyl), n is zero, 1 or 2; p is 2, 3 or 4.

6. A compound of formula (I) as claimed in claim 5 wherein $R_1$ is the group cyanomethyl, 2-isobutyrylaminoethoxy, 2-methoxy-acetylamino, isobutyrylamino methylcarbonylamino, 2-morpoholin-4-yl-ethoxy or $CH=CHR_3$, wherein $R_3$ is a t-butoxycarbonyl, carbamoyl or cyano group.

7. A compound selected from a group consisting of (±) (E)5,7-Dichloro-4-[4-(2-methoxy-acetylamino)-phenylcarbamoylmethylene]-1,2,3,4-tetrahydro-quinoline-2-carboxylic acid;

(±) (E)5,7-Dichloro-4-[4-(2-isobutyrylamino-methylcarbonylamino)-phenylcarbamoylmethylene]-1,2,3,4-tetrahydro-quinoline-2-carboxylic acid;

(±) (E)5,7-Dichloro-4-(4-cyanomethyl-phenylcarbamoylmethylene)-1,2,3,4-tetrahydro-quinoline-2-carboxylic acid;

(±) (E,E)5,7-Dichloro-4-[4-(2-cyano-vinyl)-phenylcarbamoylmethylene]-1,2,3,4-tetrahydro-quinoline-2-carboxylic acid;

(±) (E,E)4-(4-(2-tert-butoxycarbonyl-vinyl)-phenylcarbamoylmethylene]-5,7-dichloro-1,2,3,4-tetrahydro-quinoline-2-carboxylic acid;

(±) (E,E)4-[4-(2-carbamoyl-vinyl)-phenylcarbamoylmethylene]-5,7-dichloro-1,2,3,4-tetrahydro-quinoline-2-carboxylic acid;

(±) (E)5,7-Dichloro-4-[4-(2-isobutyrylamino-ethoxy)-phenylcarbamoylmethylene]-1,2,3,4-tetrahydro-quinoline-2-carboxylic acid;

(±) (E)5,7-Dichloro-4-[4-(2-morpholin-4-yl-ethoxy)-phenylcarbamoylmethylene]-1,2,3,4-tetrahydro-quinoline-2-carboxylic acid;

and physiologically acceptable salts, metabolically labile esters or enantiomers thereof.

8. A process for the preparation of a compound of claim 1 which comprises:

(a) cyclisation of a compound of formula (II)

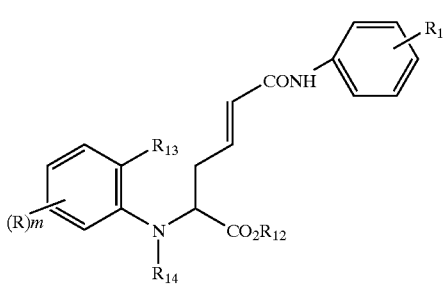

wherein R, $R_1$ and m have the meanings defined in claim 1, $R_{12}$ is a carboxyl protecting group $R_{13}$ is bromine or iodine and $R_{14}$ is hydrogen or a nitrogen protecting group;

(b) reacting an activated derivative of the carboxylic acid (III)

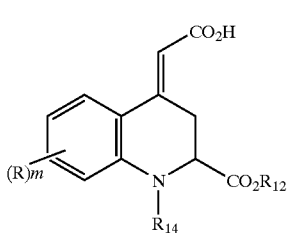

with the amine (IV)

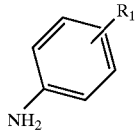

wherein R, m, $R_{12}$ and $R_{14}$ have the meanings defined above, with the amine (IV) wherein $R_1$ has the meanings defined above, optimally followed by one or more of the following steps:

1. removal of the carboxyl protecting group;
2. isolation of the compound of formula (I) as a salt thereof;
3. separation of a compound of formula (I) into a specific enantiomer thereof.

9. A pharmaceutical composition comprising a compound as claimed in claim 2 in admixture with one or more physiologically acceptable carriers or excipients.

10. A method of treatment of a mammal for a condition where antagonising the effects of excitatory amino acids on the NMDA receptor complex is of therapeutic benefit comprising administration a NMDA receptor antagonising amount of a compound as claimed in claim 2.

11. The compound according to claim 7, wherein the physiologically acceptable salt is a sodium salt.

* * * * *